(12) United States Patent
Kitami et al.

(10) Patent No.: US 7,739,920 B2
(45) Date of Patent: *Jun. 22, 2010

(54) CORIOLIS FLOWMETER HAVING A FIXING MEMBER WITH NON-PARALLEL INLET AND OUTLET PORTIONS

(75) Inventors: Hirokazu Kitami, Tokyo (JP); Yuichi Nakao, Tokyo (JP); Norio Sukemura, Tokyo (JP)

(73) Assignee: Oval Corporation, Tokyo (JP)

( * ) Notice: Subject to any disclaimer, the term of this patent is extended or adjusted under 35 U.S.C. 154(b) by 259 days.

This patent is subject to a terminal disclaimer.

(21) Appl. No.: 10/585,939

(22) PCT Filed: Sep. 24, 2004

(86) PCT No.: PCT/JP2004/014442

§ 371 (c)(1),
(2), (4) Date: Oct. 3, 2006

(87) PCT Pub. No.: WO2005/075947

PCT Pub. Date: Aug. 18, 2005

(65) Prior Publication Data

US 2007/0163363 A1 Jul. 19, 2007

(30) Foreign Application Priority Data

Feb. 3, 2004 (JP) .............................. 2004-026811

(51) Int. Cl.
*G01F 1/84* (2006.01)
(52) U.S. Cl. ................................. 73/861.355
(58) Field of Classification Search .................. None
See application file for complete search history.

(56) References Cited

U.S. PATENT DOCUMENTS

| | | | | | |
|---|---|---|---|---|---|
| 4,127,028 | A | * | 11/1978 | Cox et al. | 73/861.355 |
| 4,730,501 | A | * | 3/1988 | Levien | 73/861.357 |
| 4,825,705 | A | * | 5/1989 | Hohloch et al. | 73/861.355 |
| 5,020,375 | A | * | 6/1991 | Back-Pedersen et al. | 73/861.355 |
| 5,115,683 | A | * | 5/1992 | Pratt | 73/861.355 |
| 5,343,764 | A | * | 9/1994 | Mattar et al. | 73/861.355 |
| 5,357,811 | A | * | 10/1994 | Hoang | 73/861.355 |

(Continued)

FOREIGN PATENT DOCUMENTS

JP 04-157328 5/1992

(Continued)

*Primary Examiner*—Harshad Patel
(74) *Attorney, Agent, or Firm*—Wenderoth, Lind & Ponack, L.L.P.

(57) ABSTRACT

A first inlet portion, a second inlet portion, a first outlet portion, and a second outlet portion are fixed to a fixing member, and a connecting tube portion is provided between the first outlet portion and the second inlet portion. Further, the first inlet portion and the second inlet portion 6 are arranged in a non-parallel state such that the distance between the two increases as they depart from the fixing member. The first outlet portion and the second outlet portion are similarly arranged in a non-parallel state, the first inlet portion and the second inlet portion and the first outlet portion and the second outlet portion being arranged symmetrically. Further, the first outlet portion, the second inlet portion, and the connecting tube portion are arranged such that their three tube axes are in a straight line.

5 Claims, 11 Drawing Sheets

U.S. PATENT DOCUMENTS

| | | | | |
|---|---|---|---|---|
| 5,551,307 | A * | 9/1996 | Kane et al. | 73/861.356 |
| 5,675,093 | A * | 10/1997 | Young et al. | 73/861.355 |
| 7,409,873 | B2 * | 8/2008 | Kitami et al. | 73/861.355 |
| 7,437,950 | B2 * | 10/2008 | Nakao | 73/861.355 |

FOREIGN PATENT DOCUMENTS

| | | |
|---|---|---|
| JP | 6-7325 | 2/1994 |
| JP | 2 654 341 | 9/1997 |
| JP | 11-211529 | 8/1999 |

* cited by examiner

CORIOLIS FLOWMETER HAVING A FIXING MEMBER WITH NON-PARALLEL INLET AND OUTLET PORTIONS

BACKGROUND OF THE INVENTION

1. Technical Field

The present invention relates to a Coriolis flowmeter that is used to obtain a mass flow rate and/or density of a measurement fluid by detecting a phase difference and/or vibration frequency proportional to Coriolis forces acting on a flow tube.

2. Background Art

In a Coriolis flowmeter, a tube through which a fluid to be measured flows is supported at one end or both ends thereof, and vibration is applied to a portion of the tube around the supporting point in a direction vertical to the flowing direction of the tube (hereinafter, a tube to which vibration is applied is referred to as a flow tube). The Coriolis flowmeter is a mass flowmeter, which utilizes the fact that the Coriolis forces applied to the flow tube when vibration is thus applied thereto, are proportional to a mass flow rate. The Coriolis flowmeters are well known, and the flow tube structures thereof are roughly classified into two types: a straight tube type and a bent tube type.

In a Coriolis flowmeter of the straight tube type, when vibration is applied to a straight tube, whose both ends are supported, in a direction vertical to the straight-tube center portion axis, a difference in displacement of the straight tube due to the Coriolis forces is generated between the support portions and the central portion of the straight tube. That is, a phase difference signal is obtained, and, based on this phase difference signal, the mass flow rate is detected. The straight tube type Coriolis flowmeter thus constructed has a simple, compact, and solid structure. However, there still has a problem in that it is impossible to achieve high detection sensitivity.

In contrast, the bent tube type Coriolis flowmeter is superior to the straight tube type Coriolis flowmeter in that it allows selection of a shape for effectively obtaining the Coriolis forces. In fact, it is capable of performing mass flow rate detection with high sensitivity. Known examples of the bent tube type Coriolis flowmeter include one equipped with a single flow tube (see, for example, JP 04-055250 B), one equipped with two flow tubes arranged in parallel (see, for example, Japanese Patent No. 2939242), and one equipped with a single flow tube in a looped state (see, for example, JP 05-069453 B).

Incidentally, as a driving means for driving the flow tube, a combination of a coil and a magnet is generally employed. Regarding the mounting of the coil and the magnet, it is desirable to mount them at positions not offset with respect to the vibrating direction of the flow tube. In view of this, as disclosed in Japanese Patent No. 2939242 two flow tubes arranged in parallel are mounted so as to hold a coil and a magnet between them. Thus, a design is adopted in which the distance between the two flow tubes opposed to each other is at least large enough to enable the coil and the magnet to be held therebetween.

In the case of a Coriolis flowmeter in which two flow tubes respectively exist in planes parallel to each other and which exhibits a large caliber or high flow tube rigidity, it is necessary to enhance the power of the driving means, so that it is necessary to hold a large driving means between the two flow tubes. Thus, a design is adopted in which the distance between the flow tubes is of necessity large even at the fixing end portions constituting the roots of the flow tubes.

However, an increase in the above-mentioned distance at the fixing end portions involves the following problem: it leads to a deficiency in rigidity at the fixing end portions, with the result that vibration leakage is likely to occur (the flow tubes vibrate owing to bending vibration, and then the vibration leaks out).

On the other hand, in the construction as disclosed in JP 05-69453 B, in which a single flow tube is looped, another problem is involved: as shown in FIGS. 11 and 12, it is necessary for a bent tube portion 101 to exist between a first curved tube portion 102 and a second curved tube portion 103. Because of that necessity, the quick manufacture of the bends shown in the figure is rather difficult and, further, there is a problem in terms of the resistance to pressure of the tubes.

SUMMARY OF THE INVENTION

The present invention has been made in view of the above problems in the prior art. It is an object of the present invention to provide a Coriolis flowmeter which is not susceptible to vibration leakage, and which is easy to manufacture and provides high durability.

Figure 1:
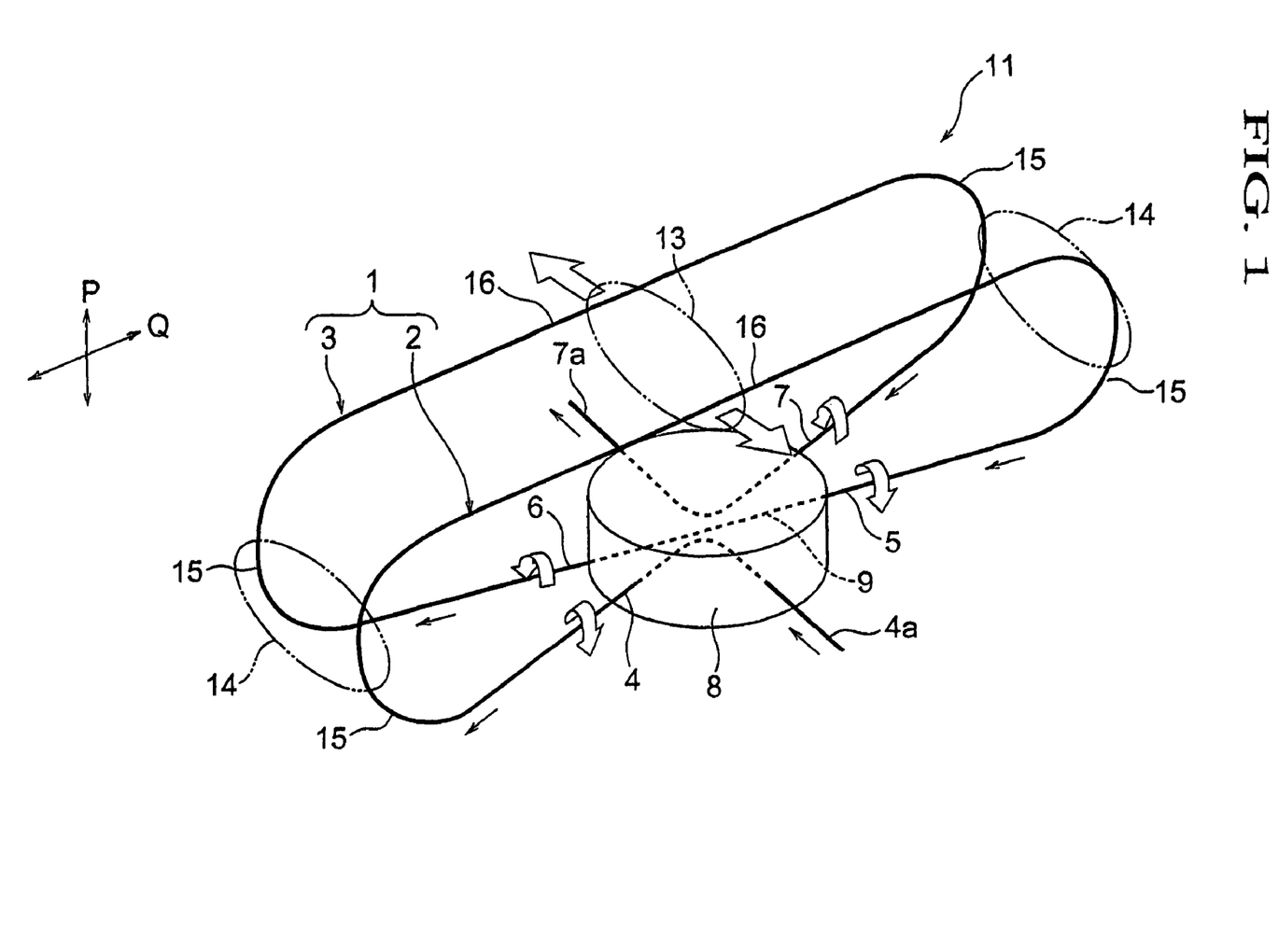
FIG. 1 is a schematic view of a Coriolis flowmeter according to an embodiment of the present invention, for showing the basic construction of a main portion of the Coriolis flowmeter.

To attain the object of the present invention, there is provided, as shown in FIG. 1 illustrative of its basic construction, a Coriolis flowmeter 11 for obtaining at least one of a mass flow rate and a density of a measurement fluid through detection of at least one of a phase difference and a vibration frequency proportional to the Coriolis forces acting on a pair of first and second curved tube portions 2 and 3 constituting a measurement flow tube 1 by vibrating the first and second curved tube portions 2 and 3 while being opposed to each other, including: a first inlet portion 4 through which the measurement fluid flows in and a first outlet portion 5 through which the measurement fluid flows out, in the first curved tube portion 2; and a second inlet portion 6 through which the measurement fluid flows in and a second outlet portion 7 through which the measurement fluid flows out, in the second curved tube portion 3. A fixing member 8 is provided so as to be situated in a middle position of the flow tube 1 as seen in plan view. The first inlet portion 4, the second inlet portion 6, the first outlet portion 5, and the second outlet portion 7 are fixed to the fixing member 8. In the fixation to the fixing member 8, tube axes of the first inlet portion 4, the second inlet portion 6, the first outlet portion 5, and the second outlet portion 7 are arranged in the same plane, the first inlet portion 4 and the second inlet portion 6 are arranged in a non-parallel state such that a distance therebetween increases as they depart from the fixing member 8, the first outlet portion 5 and the second outlet portion 7 are arranged in a non-parallel state such that a distance therebetween increases as they depart from the fixing member 8, and the first inlet portion 4 and the second inlet portion 6, and the first outlet portion 5 and the second outlet portion 7 are arranged symmetrically.

Further, to attain the object of the present invention, there is provided, as shown in FIG. 1, a Coriolis flowmeter 11 for obtaining at least one of a mass flow rate and a density of a measurement fluid through detection of at least one of a phase difference and a vibration frequency proportional to the Coriolis forces acting on a pair of first and second curved tube portions 2 and 3 constituting a measurement flow tube 1 by vibrating the first and second curved tube portions 2 and 3 while being opposed to each other, including: a first inlet portion 4 through which the measurement fluid flows in and a first outlet portion 5 through which the measurement fluid flows out, in the first curved tube portion 2; and a second inlet portion 6 through which the measurement fluid flows in and a second outlet portion 7 through which the measurement fluid flows out, in the second curved tube portion 3. A fixing member 8 is provided so as to be situated in a middle position of the flow tube 1 as seen in plan view; the first inlet portion 4, the second inlet portion 6, the first outlet portion 5, and the second outlet portion 7 are fixed to the fixing member 8; and a connecting tube portion 9 is provided between the first outlet portion 5 and the second inlet portion 6, for connecting the two portions. In the fixation to the fixing member 8, the first inlet portion 4 and the second inlet portion 6 are arranged in a non-parallel state such that a distance therebetween increases as they depart from the fixing member 8, the first outlet portion 5 and the second outlet portion 7 are arranged in a non-parallel state such that a distance therebetween increases as they depart from the fixing member 8, and the first inlet portion 4 and the second inlet portion 6, and the first outlet portion 5 and the second outlet portion 7 are arranged symmetrically; and the first outlet portion 5, the second inlet portion 6, and the connecting tube portion 9 are arranged such that tube axes of the three portions are in a straight line.

Further, to attain the object of the present invention, in the Coriolis flowmeter, the fixing member 8 is formed substantially in a circular configuration or an arcuate configuration in plan view.

Further, to attain the object of the present invention, the fixing member 8 is formed in a wall-like configuration.

Due to this construction, when the first curved tube portion 2 and the second curved tube portion 3 are vibrated while opposed to each other (FIG. 1 shows the state where a repulsive action is generated in the driving means; in the case of an attracting action, the directions of the arrows in FIG. 1 are reversed), the fixing member 8, to which the first inlet portion 4, the second inlet portion 6, the first outlet portion 5, and the second outlet portion 7 are fixed, receives at each fixing portion a torsional stress due to a torsional vibration converted from a bending vibration.

However, as shown in FIG. 1, the first inlet portion 4 and the second inlet portion 6 are not parallel to each other, and the first outlet portion 5 and the second outlet portion 7 are not parallel to each other, either. Further, the first inlet portion 4 and the second inlet portion 6, and the first outlet portion 5 and the second outlet portion 7 are in symmetrical positional relationships. Thus, when the first curved tube portion 2 and the second curved tube portion 3 are vibrated while opposed to each other, the torsional stress due to the first inlet portion 4 and the second outlet portion 7 is canceled by these two, and the torsional stress due to the second inlet portion 6 and the first outlet portion 5 is also canceled by these two. As a result, substantially no vibration is generated in the fixing member 8, and the loads applied to the first inlet portion 4, the second inlet portion 6, the first outlet portion 5, and the second outlet portion 7 are reduced.

Accordingly, according to the present invention, even if the rigidity of the fixing member 8 is low, and if the mass is small, it is possible to effectively restrain vibration leakage. Further, as shown in FIG. 1, the first outlet portion 5, the second inlet portion 6, and the connecting tube portion 9 are arranged continuously in a straight line, so that, according to the present invention, it is possible to enhance the productivity and durability of a Coriolis flowmeter.

According to the present invention, it is possible to provide a Coriolis flowmeter which is not subject to vibration leakage.

According to the present invention, it is possible to provide a Coriolis flowmeter which is not subject to vibration leakage, and which is easy to manufacture and provides high durability.

According to the present invention, uniform fixation is possible in the flow tube circumferential direction, so that it is possible to provide a Coriolis flowmeter which is more resistant to vibration leakage.

According to the present invention, it is possible to achieve a reduction in the weight and cost of a Coriolis flowmeter.

BRIEF DESCRIPTION OF THE DRAWINGS

FIG. 3 is a diagram for comparing conventional Coriolis flowmeters with that of the present invention, in which FIG. 3(*a*) shows the type in which the inlet portions and the outlet portions are directed upwards as seen in the drawing, and FIG. 3(*b*) shows the type in which the inlet portions and the outlet portions are directed horizontally as seen in the drawing.

FIG. 4 is a diagram showing a first embodiment of the present invention, in which FIG. 4(*a*) is a main portion front view, FIG. 4(*b*) is a sectional view taken along the line A1-A1 of FIG. 4(*a*), FIG. 4(*c*) is a sectional view taken along the line B1-B1 of FIG. 4(*a*), and FIG. 4(*d*) is a side view of FIG. 4(*a*).

FIG. 5 is a diagram showing a second embodiment of the present invention, in which FIG. 5(*a*) is a main portion front view, FIG. 5(*b*) is a sectional view taken along the line A2-A2 of FIG. 5(*a*), FIG. 5(*c*) is a sectional view taken along the line B2-B2 of FIG. 5(*a*), and FIG. 5(*d*) is a side view of FIG. 5(*a*).

FIG. 6 is a diagram showing a third embodiment of the present invention, in which FIG. 6(*a*) is a main portion front view, FIG. 6(*b*) is a sectional view taken along the line A3-A3 of FIG. 6(*a*), FIG. 6(*c*) is a sectional view taken along the line B3-B3 of FIG. 6(*a*), and FIG. 6(*d*) is a side view of FIG. 6(*a*).

FIG. 7 is a diagram showing a fourth embodiment of the present invention, in which FIG. 7(*a*) is a main portion front view, FIG. 7(*b*) is a sectional view taken along the line A4-A4 of FIG. 7(*a*), FIG. 7(*c*) is a sectional view taken along the line B4-B4 of FIG. 7(*a*), and FIG. 7(*d*) is a side view of FIG. 7(*a*).

FIG. 8 is a diagram showing a fifth embodiment of the present invention, in which FIG. 8(*a*) is a main portion front view, FIG. 8(*b*) is a sectional view taken along the line A5-A5 of FIG. 8(*a*), FIG. 8(*c*) is a sectional view taken along the line B5-B5 of FIG. 8(*a*), and FIG. 8(*d*) is a side view of FIG. 8(*a*).

FIG. 9 is a diagram showing a sixth embodiment of the present invention, in which FIG. 9(*a*) is a main portion front view, FIG. 9(*b*) is a sectional view taken along the line A6-A6 of FIG. 9(*a*), FIG. 9(*c*) is a sectional view taken along the line B6-B6 of FIG. 9(*a*), and FIG. 9(*d*) is a side view of FIG. 9(*a*).

FIG. 11 is a perspective view of the flow tubes of a conventional Coriolis flowmeter.

FIG. 12 is a plan view of the flow tubes of FIG. 11.

DETAILED DESCRIPTION OF THE INVENTION

In the following, the present invention will be described with reference to the drawings.

FIG. 1 is a schematic view of a Coriolis flowmeter according to an embodiment of the present invention, for showing the basic construction of a main portion of the Coriolis flowmeter.

Figure 2:
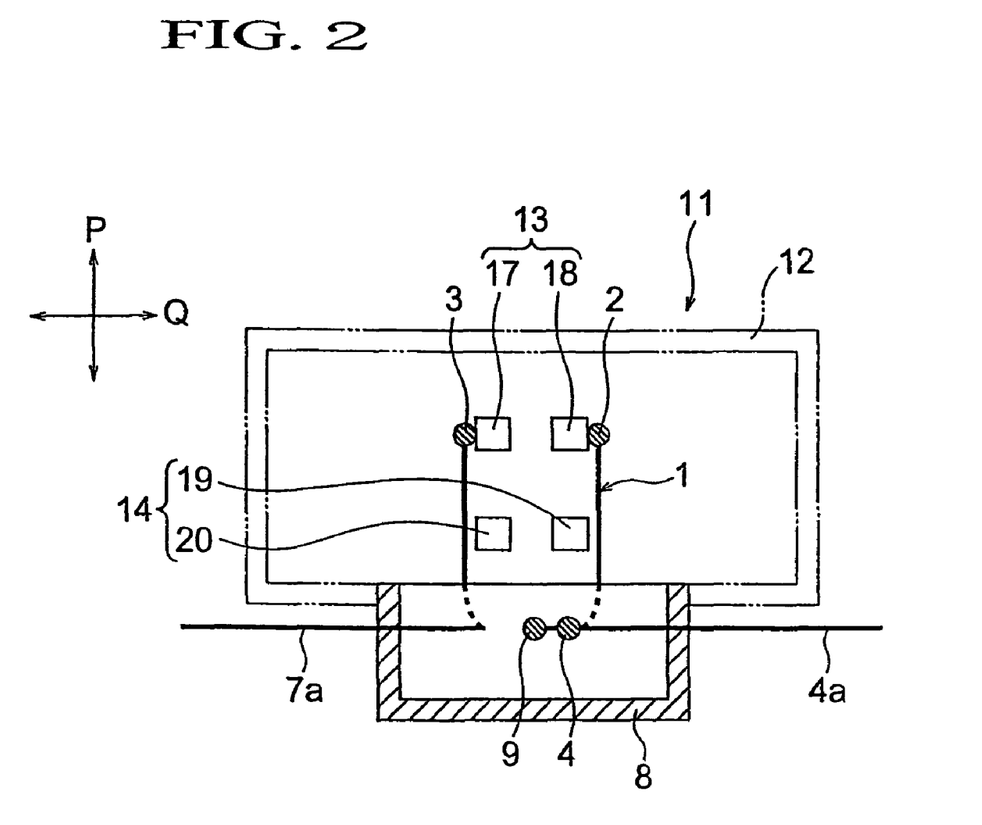
FIG. 2 is a longitudinal sectional view of the central portion (including the casing) of the Coriolis flowmeter of FIG. 1.

Further, FIG. 2 is a longitudinal sectional view of the central portion (including the casing) of the Coriolis flowmeter of FIG. 1.

In FIGS. 1 and 2, a Coriolis flowmeter 11 according to the present invention includes a casing 12, a single flow tube 1 (hereinafter, this is referred to as a flow tube) accommodated in the casing 12, a drive device 13, a sensor portion (not shown) having a pair of vibration detecting sensors 14 and 14 and a temperature sensor (not shown), a signal computation processing portion (not shown) for performing computation processing on a mass flow rate, etc. based on a signal from the sensor portion, and an excitation circuit portion (not shown) for exciting the drive device 13.

In the following, those components will be described.

The casing 12 has a structure resistant to bending and torsion. Further, the casing 12 is formed in a size large enough to accommodate the flow tube 1, with a fixing member 8 for fixing the flow tube 1 in position being mounted thereto. Further, the casing 12 is formed so as to be capable of protecting the main portion of the flowmeter including the flow tube 1. The casing 12 is filled with an inert gas, such as argon gas. Due to the filling with the inert gas, condensation on the flow tube 1, etc. is prevented.

Figure 10:
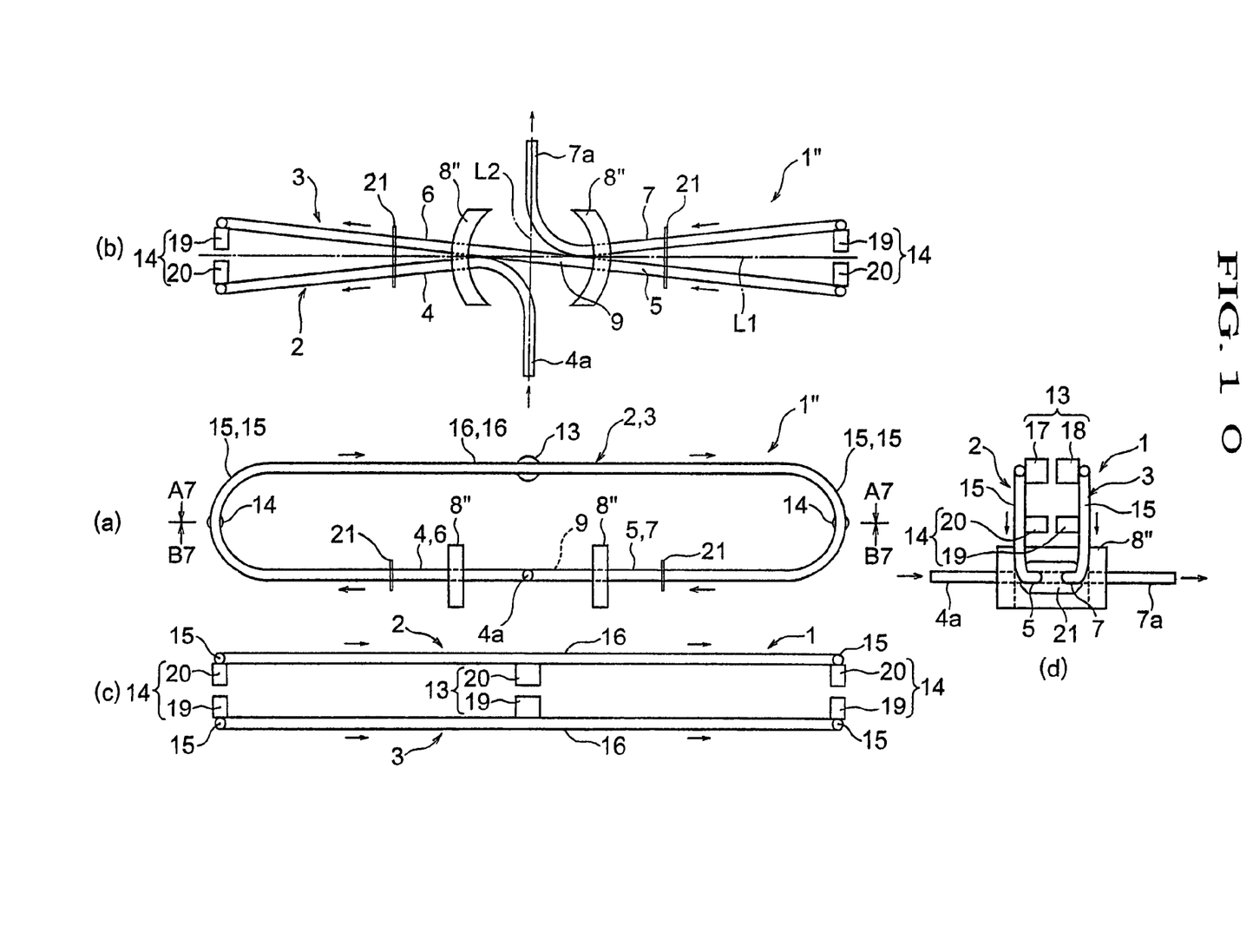
FIG. 10 is an explanatory view showing another example of the shape of the fixing member, in which FIG. 10(*a*) is a front view of a Coriolis flowmeter, FIG. 10(*b*) is a sectional view taken along the line A7-A7 of FIG. 10(*a*), FIG. 10(*c*) is a sectional view taken along the line B7-B7 of FIG. 10(*a*), and FIG. 10(*d*) is a side view of FIG. 10(*a*).

The casing 12 is mounted to the fixing member 8 by an appropriate means. The fixing member 8 is formed in a circular configuration in plan view. Although desirable, it is not always necessary for the fixing member 8 to be of a circular configuration in plan view. That is, for example, it may be formed as a fixing member of a rectangular configuration in plan view or, as shown in FIG. 10, it may be formed as arcuate fixing members 8" of a Coriolis flowmeter 1". Further, in this embodiment, the fixing member 8 is formed as a wall member defining an inner space.

The flow tube 1 consists of a single looped measurement conduit (it is not always necessary for the flow tube 1 to consist of a single looped conduit, as described in detail below with reference to a sixth embodiment of the present invention), and includes a first curved tube portion 2 and a second curved tube portion 3 arranged so as to be opposed to each other, and a connecting tube portion 9 connecting the first curved tube portion 2 and the second curved tube portion 3 to each other. Assuming that the arrow P and the arrow Q in FIG. 1 respectively indicate the vertical direction and the horizontal direction, the first curved tube portion 2 and the second curved tube portion 3 are formed substantially in an elliptical configuration, with both being elongated in the horizontal direction.

The first curved tube portion 2 has a first inlet portion 4 through which a measurement fluid flows in and a first outlet portion 5 through which the measurement fluid flows out. The second curved tube portion 3 has a second inlet portion 6 through which a measurement fluid flows in and a second outlet portion 7 through which the measurement fluid flows out. The connecting tube portion 9 is provided between the first outlet portion 5 and the second inlet portion 6. In other words, the connecting tube portion 9 is provided for the purpose of connecting the first outlet portion 5 and the second inlet portion 6 to each other. The first outlet portion 5, the second inlet portion 6, and the connecting tube portion 9 are formed and arranged such that they are continuously connected together in a straight line, in other words, that the axes of the three tubes are in a straight line.

The first inlet portion 4, the second inlet portion 6, the first outlet portion 5, and the second outlet portion 7 are fixed to the fixing member 8. The first inlet portion 4 and the second inlet portion 6 are fixed and arranged in a non-parallel state such that the distance between them increases as they depart from the fixing member 8. Similarly, the first outlet portion 5 and the second outlet portion 7 are fixed and arranged in a non-parallel state such that the distance between them increases as they depart from the fixing member 8. Further, the first inlet portion 4 and the second inlet portion 6, and the first outlet portion 5 and the second outlet portion 7 are fixed and arranged so as to be in symmetrical positional relationships.

Here, by looking at a state where the first inlet portion 4, the second inlet portion 6, the first outlet portion 5, and the second outlet portion 7 are fixed to the fixing member 8, it can be recognized that they are fixed in the same plane. However, the way in which the first inlet portion 4, the second inlet portion 6, the first outlet portion 5, and the second outlet portion 7 are fixed to the fixing member 8 is not restricted to this. For example, the fixation to the fixing member 8 may also be effected such that the first inlet portion 4 and the second outlet portion 7 are in the same plane and that the first outlet portion 5 and the second inlet portion 6 are in the same plane.

A terminal 4a of the first inlet portion 4 is led to the exterior in order to allow inflow of a measurement fluid. Further, like the terminal 4a, a terminal 7a of the second outlet portion 7 is led to the exterior in order to allow outflow of the measurement fluid. The terminal 4a and the terminal 7a are led out so as to be perpendicular to the arrow P of FIG. 1 and as to be opposite to each other. A measurement fluid flowing in through the terminal 4a of the first inlet portion 4 passes through the first curved tube portion 2, the connecting tube portion 9, and the second curved tube portion 3 before flowing out through the terminal 7a of the second outlet portion 7 (as for the flow of the measurement fluid, see the arrows in FIG. 1).

The first curved tube portion 2 has, in addition to the first inlet portion 4 and the first outlet portion 5, substantially arcuate curved portions 15 and 15 and a straight apex portion 16. Similarly, the second curved tube portion 3 has, in addition to the second inlet portion 6 and the second outlet portion 7, substantially arcuate curved portions 15 and 15 and a straight apex portion 16.

The apex portion 16 of the first curved tube portion 2 and the apex portion 16 of the second curved tube portion 3 are arranged in parallel with a gap therebetween large enough to hold the driving device 13. Similarly, the curved portions 15 and 15 of the first curved tube portion 2, and the curved portions 15 and 15 of the second curved tube portion 3 are arranged with a gap therebetween large enough to hold the vibration detecting sensors 14 and 14. The first inlet portion 4 and the second inlet portion 6 are formed and arranged such that the distance therebetween is large at the position corresponding to the curved portions 15 and 15 and that the distance therebetween is small at the position corresponding to the fixing member 8. Similarly, the first outlet portion 5 and the second outlet portion 7 are formed and arranged such that the distance therebetween is large at the position corresponding to the curved portions 15 and 15 and that the distance therebetween is small at the position corresponding to the fixing member 8.

Since the distance between the first inlet portion 4 and the second inlet portion 6 is small at the fixing member 8, vibration leakage does not easily occur. Further, as described below, a structure is adopted which cancels a torsional stress. Substantially no vibration is generated in the fixing member 8.

Note that, the material of the flow tube 1 is one usually adopted in this technical field, such as stainless steel, hastelloy, or titanium alloy.

The driving device 13 constituting the sensor portion causes the first curved tube portion 2 and the second curved tube portion 3 of the flow tube 1 to vibrate while opposed to each other, and is equipped with a coil 17 and a magnet 18. The driving device 13 is arranged at the center of the apex portions 16 and 16 of the flow tube 1 and so as to be held between them. In other words, the driving device 13 is mounted at a position not offset with respect to the vibrating direction of the flow tube 1.

The coil 17 of the driving device 13 is mounted to one apex portion 16 of the flow tube 1 by using a dedicated mounting tool. Further, although not particularly shown, an FPC (flexible printed circuit) or electric wire is led out from the coil 17. The magnet 18 of the driving device 13 is mounted to the other apex portion 16 of the flow tube 1 by using a dedicated mounting tool.

When an attracting action is generated in the driving device 13, the magnet 18 is inserted into the coil 17, with the result that the apex portions 16 and 16 of the flow tube 1 are brought close to each other. In contrast, when a repulsive action is generated, the apex portions 16 and 16 of the flow tube 1 are moved away from each other. Since the flow tube 1 is fixed to the fixing member 8 as described above, the driving device 13 is constructed to alternately drive the flow tube 1 in the rotating direction around the fixing member 8.

The vibration detecting sensors 14 and 14 constituting the sensor portion are sensors for detecting vibration of the flow tube 1 and for detecting a phase difference proportional to the Coriolis forces acting on the flow tube 1, and are each equipped with a coil 19 and a magnet 20 (The sensors are not restricted to the ones as described above; they may also be such as acceleration sensors, optical means, or capacitance type or distortion type (piezoelectric type) means as long as they are capable of detecting one of displacement, velocity, and acceleration).

The vibration detecting sensors 14 and 14 thus constructed are arranged, for example, at positions within a range where they are held between the curved portions 15 and 15 of the flow tube 1 and where they can detect the phase difference proportional to the Coriolis force.

The respective coils 19 of the vibration detecting sensors 14 and 14 are mounted to one curved portion 15 of the flow tube 1 by using a dedicated mounting tool. Further, although not particularly shown, FPCs (flexible printed circuits) or electric wires are led out from the coils 19. The respective magnets 20 of the vibration detecting sensors 14 and 14 are mounted to the other curved portion 15 of the flow tube 1 by using a dedicated mounting tool.

Although not particularly shown, a board or the like is provided inside the Coriolis flowmeter 11 of the present invention. Further, connected to the board is a wire harness led out to the exterior of the casing 12.

The temperature sensor constituting a part of the sensor portion serves to effect temperature compensation on the Coriolis flowmeter 11, and is mounted to the flow tube 1 by an appropriate means. More specifically, it is mounted, for example, to the first inlet portion 4. Further, an FPC (flexible printed circuit) or electric wire (not shown), led out from the temperature sensor, is connected to the board.

Wiring and connection are effected in the signal computation processing portion such that there are input thereto a detection signal from one vibration detecting sensor 14 regarding deformation of the flow tube 1, a detection signal from the other vibration detecting sensor 14 regarding deformation of the flow tube 1, and a detection signal from the temperature sensor regarding the temperature of the flow tube 1. In this signal computation processing portion, computation on a mass flow rate and a density is effected based on the detection signals input from the sensor portion. Further, in the signal computation processing portion, the mass flow rate and density obtained through computation are displayed on a display (not shown).

The excitation circuit portion includes a smoothing portion, a comparing portion, a target setting portion, a variable amplification portion, and a drive output portion. Wiring is effected in the smoothing portion so that a detection signal from one vibration detecting sensor 14 (or the other vibration detecting sensor 14) may be extracted. Further, the smoothing portion has a function by which it can rectify and smooth the input detection signal and output a DC voltage proportional to the amplitude thereof. The comparing portion has a function by which it can compare the DC voltage from the smoothing portion with a target set voltage output from the target setting portion and control the gain of the variable amplification portion to control the amplitude of the resonance vibration in conformity with the target set voltage.

In the above construction, when a measurement fluid is caused to flow through the flow tube 1, and the driving device 13 is driven to cause the first curved tube portion 2 and the second curved tube portion 3 to vibrate while opposed to each other, due to a difference in phase generated by the Coriolis force at the vibration detecting sensors 14 and 14, the mass flow rate is calculated by the signal computation processing portion. Further, in this embodiment, the density is also calculated from the vibration frequency.

Figure 3:
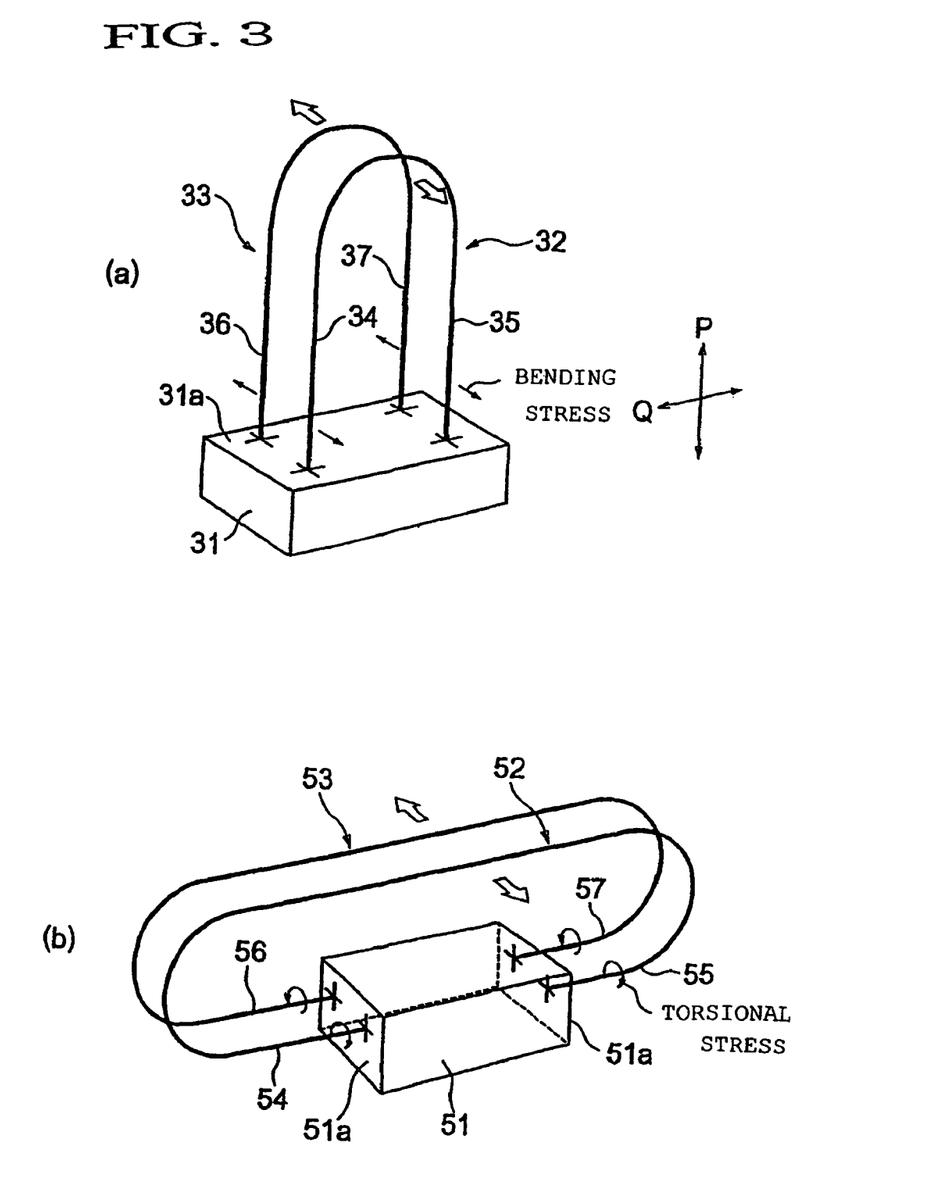

Here, the superiority of the Coriolis flowmeter 11 of the present invention to the conventional ones as shown in FIGS. 3(*a*) and 3(*b*) will be clarified with reference to FIG. 3. Note that, in FIG. 3, the arrow P indicates the vertical direction, and the arrow Q indicates the horizontal direction.

In FIG. 3(*a*), fixed to a fixing member 31 are a first curved tube portion 32 and a second curved tube portion 33 constituting a flow tube. The first curved tube portion 32 and the second curved tube portion 33 are both formed in a reverse-U-shaped configuration and are arranged so as to be opposed to each other. The plane as defined by the first curved tube portion 32 and the plane as defined by the second curved tube portion 33 are parallel to each other. Formed in the first curved tube portion 32 are a first inlet portion 34 through which the measurement fluid flows in and a first outlet portion 35 through which measurement fluid flow out. Formed in the second curved tube portion 33 are a second inlet portion 36 through which the measurement fluid flows in and a second outlet portion 37 through which the measurement fluid flows out. The first inlet portion 34, the first outlet portion 35, the second inlet portion 36, and the second outlet portion 37 extend in the vertical direction, and are secured to an upper surface 31*a* of the fixing member 31 so as to be perpendicular thereto.

When, in the above construction, driving is effected between the apex portions of the first curved tube portion 32 and the second curved tube portion 33 to cause the first curved tube portion 32 and the second curved tube portion 33 to vibrate while opposed to each other (FIG. 3(*a*) shows a state in which a repulsive action of the driving device is generated; in the case of an attracting action, the arrows are reversed; this also applies to FIG. 3(b)), bending stresses as indicated by the arrows in FIG. 3(a) are generated. The bending stresses have the effect of causing the fixing portions of the first inlet portion 34, the first outlet portion 35, the second inlet portion 36, and the second outlet portion 37 to vibrate in the vertical direction. When the distance between the first inlet portion 34 and the second inlet portion 36 and the distance between the first outlet portion 35 and the second outlet portion 37 are relatively large, vibration leakage may occur due to the above-mentioned vibration in the vertical direction.

In FIG. 3(b), fixed to a fixing member 51 are a first curved tube portion 52 and a second curved tube portion 53 constituting a flow tube. The first curved tube portion 52 and the second curved tube portion 53 are both formed as ellipses extending in the horizontal direction and arranged so as to be opposed to each other. The plane as defined by the first curved tube portion 52 and the plane as defined by the second curved tube portion 53 are parallel to each other. The first curved tube portion 52 has a first inlet portion 54 through which the measurement fluid flows in and a first outlet portion 55 through which the measurement fluid flows out. The second curved tube portion 53 has a second inlet portion 56 through which the measurement fluid flows in and a second outlet portion 57 through which the measurement fluid flows out. The first inlet portion 54, the first outlet portion 55, the second inlet portion 56, and the second outlet portion 57 extend in the horizontal direction, and are fixed to side surfaces 51a and 51a of the fixing member 51 so as to be perpendicular thereto.

In the above construction, when driving is effected between the apex portions of the first curved tube portion 52 and the second curved tube portion 53 to cause the first curved tube portion 52 and the second curved tube portion 53 to vibrate while opposed to each other, torsional stresses as indicated by the arrows in FIG. 3(b) are generated. In the type as shown in FIG. 3(b), bending vibration to be converted to torsional vibration, with the result that a torsional stress is generated. Thus, it is to be assumed that there occurs no vibration leakage due to the vertical vibration as mentioned above. However, the torsional stress due to the first inlet portion 54 and the torsional stress due to the first outlet portion 55 are torsional stresses in the same direction, and, further, the torsional stress due to the second inlet portion 56 and the torsional stress due to the second outlet portion 57 are torsional stresses in the same direction, so that curving deflection may occur in the fixing member 51.

Referring again to FIG. 1, when the first curved tube portion 2 and the second curved tube portion 3 of the Coriolis flowmeter 11 of the present invention are vibrated while opposed to each other (FIG. 1 shows a state in which the repulsive action of the driving device 13 is generated; in the case of the attracting action, the arrows in FIG. 1 are reversed), there are applied, to the fixing member 8 to which the first inlet portion 4, the second inlet portion 6, the first outlet portion 5, and the second outlet portion 7 are fixed, torsional stresses due to the torsional vibration converted from the bending vibration at each fixing portion. However, as shown in FIG. 1, the first inlet portion 4 and the second inlet portion 6 are not parallel to each other, and the first outlet portion 5 and the second outlet portion 7 are not parallel to each other, either. Further, the first inlet portion 4 and the second inlet portion 6, and the first outlet portion 5 and the second outlet portion 7 are in symmetrical positional relationships, so that the torsional stresses due to the first inlet portion 4 and the second outlet portion 7 are canceled therebetween, and the torsional stresses due to the second inlet portion 6 and the first outlet portion 5 are also canceled therebetween. Thus, substantially no vibration is generated in the fixing member 8.

According to the present invention, the loads on the first inlet portion 4, the second inlet portion 6, the first outlet portion 5, and the second outlet portion 7 are small. Even if the rigidity of the fixing member 8 is low, or if the mass is small, it is possible to effectively restrain vibration leakage. Further, as shown in FIG. 1, the first outlet portion 5, the second inlet portion 6, and the connecting tube portion 9 are arranged continuously in a straight line, so that, according to the present invention, it is possible to enhance the ease of manufacture and durability of a Coriolis flowmeter.

As described above, according to the present invention, it is possible to provide the Coriolis flowmeter 11, which is not subject to vibration leakage, and which is easy to manufacture and provides high durability.

Next, more specific examples of the configuration of the main portion of the Coriolis flowmeter will be described with reference to FIGS. 4 through 9.

Example 1

In FIG. 4(a) through 4(d), the flow tube 1 is obtained by looping a single measurement flow tube, and includes the first curved tube portion 2 and the second curved tube portion 3 arranged so as to be opposed to each other, and the connecting tube portion 9 connecting the first curved tube portion 2 and the second curved tube portion 3 to each other. In the flow tube 1 shown in FIGS. 4(a) through 4(d), the flow tube 1 as described with reference to FIG. 1 is embodied. In the following, its construction will be briefly described.

Figure 4:
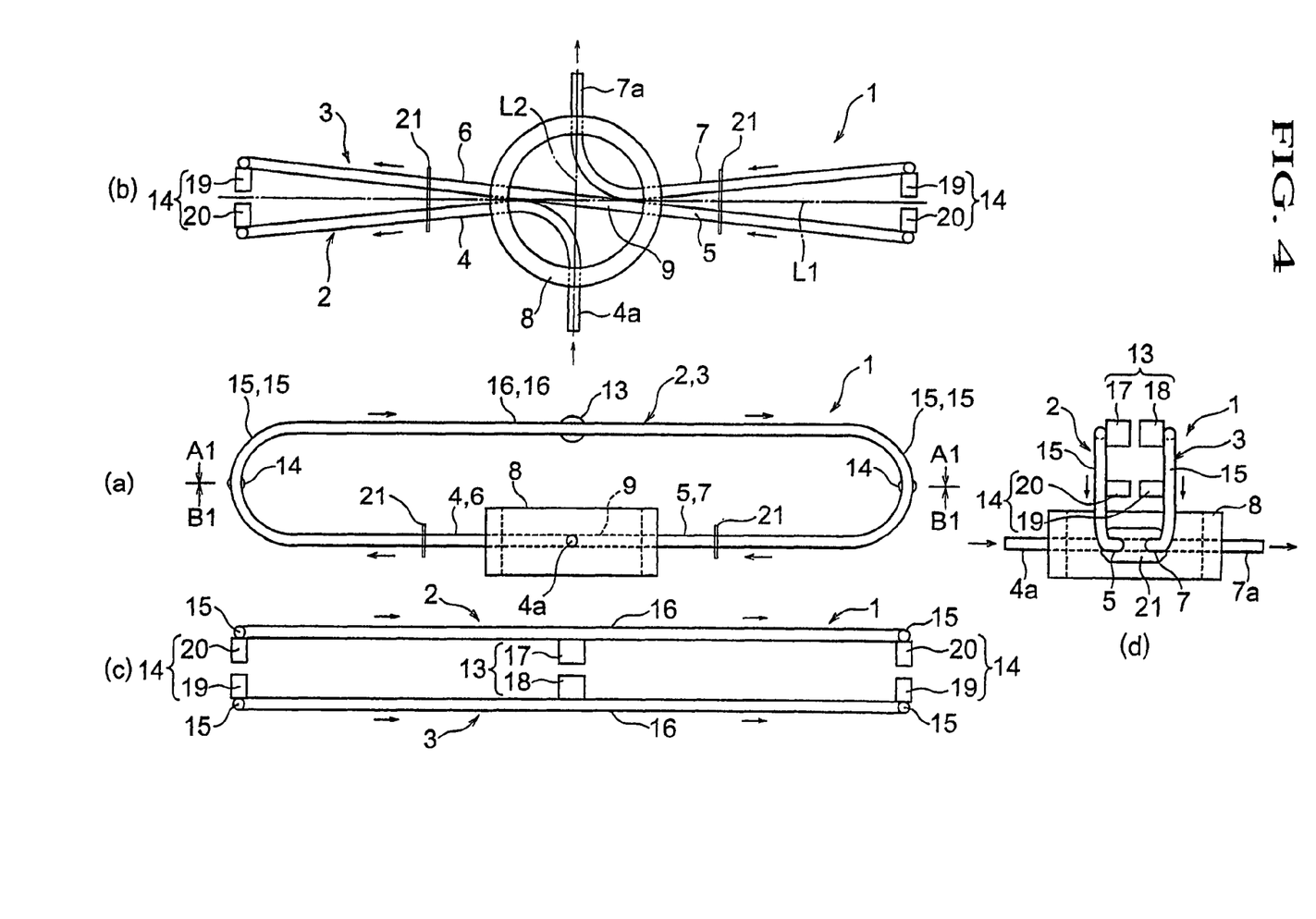

The first curved tube portion 2 has the first inlet portion 4 and the first outlet portion 5. The second curved tube portion 3 has the second inlet portion 6 and the second outlet portion 7. The connecting tube portion 9 is provided between the first outlet portion 5 and the second inlet portion 6. The first outlet portion 5, the second inlet portion 6, and the connecting tube portion 9 are formed and arranged so as to be continuous in a straight line.

The first inlet portion 4 and the second inlet portion 6 are fixed to the fixing member 8 so as to be in the same plane; and the first inlet portion 4 and the second inlet portion 6 are arranged so as not to be parallel to each other. Like the first inlet portion 4 and the second inlet portion 6, the first outlet portion 5 and the second outlet portion 7 are fixed to the fixing member 8 so as to be in the same plane, with the first outlet portion 5 and the second outlet portion 7 being arranged so as not to be parallel to each other. The terminal 4a of the first inlet portion 4 and the terminal 7a of the second outlet portion 7 are led out such that, as shown in FIG. 4(a), they are perpendicular to the arrow P of FIG. 1 and that the direction in which the measurement fluid flows in (terminal 4a) and the direction in which the measurement fluid flows out (terminal 7a) are opposite to each other.

The driving device 13 is provided between the respective apex portions 16 and 16 of the first curved tube portion 2 and the second curved tube portion 3. Further, between the respective curved portions 15 and 15 of the first curved tube portion 2 and the second curved tube portion 3, there are provided the vibration detecting sensors 14 and 14. A well-known brace bar 21 is provided so as to be astride the first inlet portion 4 and the second inlet portion 6. Similarly, another well-known brace bar 21 is provided so as to be astride the first outlet portion 5 and the second outlet portion 7. The brace bars 21 are spaced apart from the fixing member 8 by a predetermined distance. The arrows in the figures show how the measurement fluid flows.

Example 2

Figure 5:
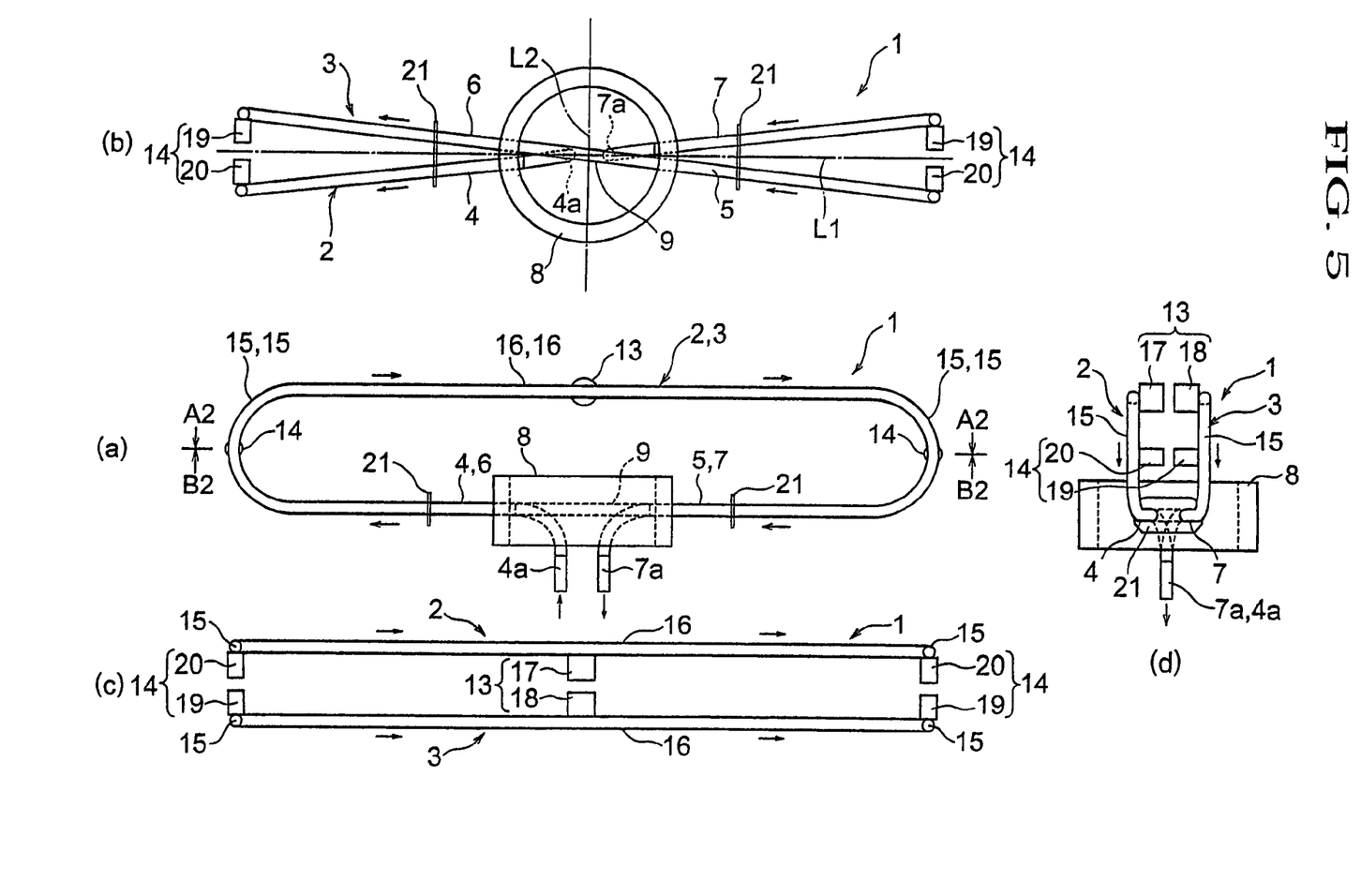

In the flow tube 1 shown in FIGS. 5(a) through 5(d), the lead-out directions of the terminal 4a of the first inlet portion 4 and the terminal 7a of the second outlet portion 7 of the flow tube 1 shown in FIGS. 4(a) through 4(d) are changed. Thus, the terminal 4a of the first inlet portion 4 and the terminal 7a of the second outlet portion 7 shown in FIG. 5 are led out such that, as shown in FIG. 5(a), the direction in which the measurement fluid flows in (terminal 4a) and the direction in which the measurement fluid flows out (terminal 7a) are the same (the vertical direction: see the arrow P of FIG. 1). Further, the terminal 4a of the first inlet portion 4 and the terminal 7a of the second outlet portion 7 are led out so as to be arranged in the center line L1 of the first curved tube portion 2 and the second curved tube portion 3 as shown in FIG. 5(b).

Example 3

Figure 6:
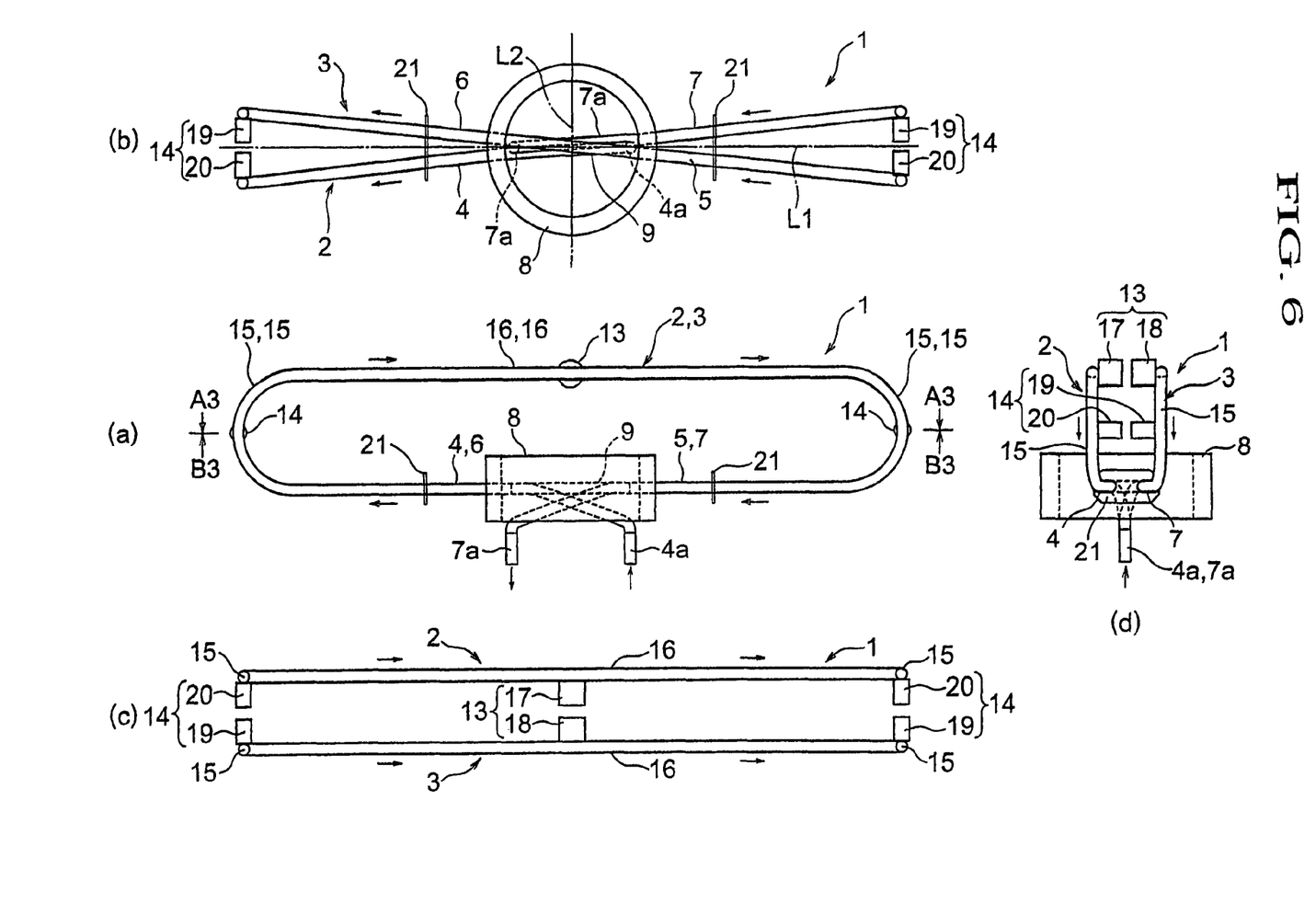

In the flow tube 1 shown in FIGS. 6(a) through 6(d), the lead-out directions of the terminal 4a of the first inlet portion 4 and the terminal 7a of the second outlet portion 7 of the flow tube 1 shown in FIGS. 4(a) through 4(d) are changed. Thus, the terminal 4a of the first inlet portion 4 and the terminal 7a of the second outlet portion 7 shown in FIG. 6 are led out such that, as shown in FIG. 6(a), the direction in which the measurement fluid flows in (terminal 4a) and the direction in which the measurement fluid flows out (terminal 7a) are the same (the vertical direction: see the arrow P of FIG. 1). Further, the first curved tube portion 2 with the terminal 4a of the first inlet portion 4 and the second curved tube portion 3 with the terminal 7a of the second outlet portion 7 cross each other as shown in FIG. 6(a), and, in this state, they are led out so as to be arranged in the center line L1 of the first curved tube portion 2 and the second curved tube portion 3 as shown in FIG. 6(b).

Example 4

Figure 7:
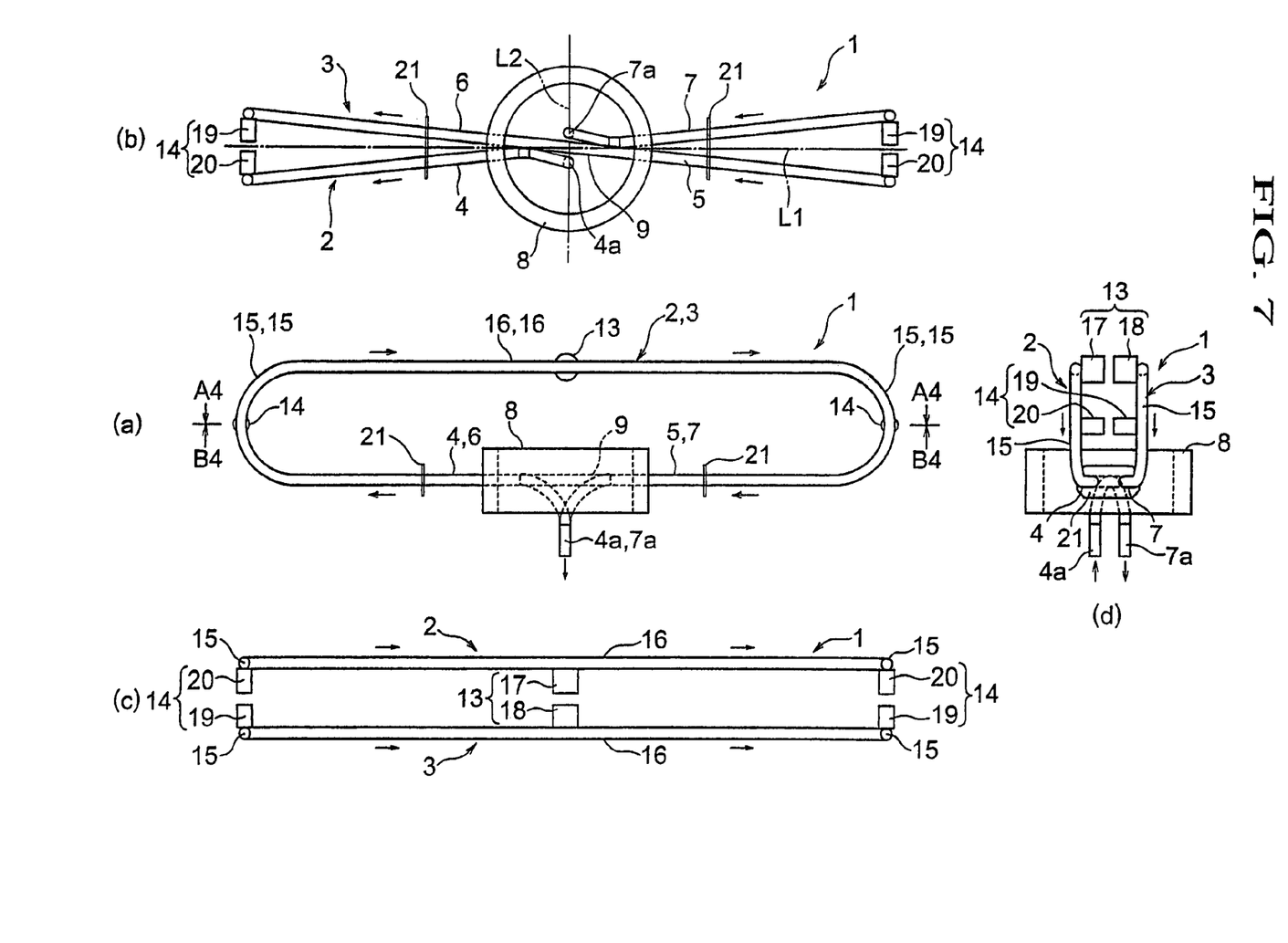
Figure 8:
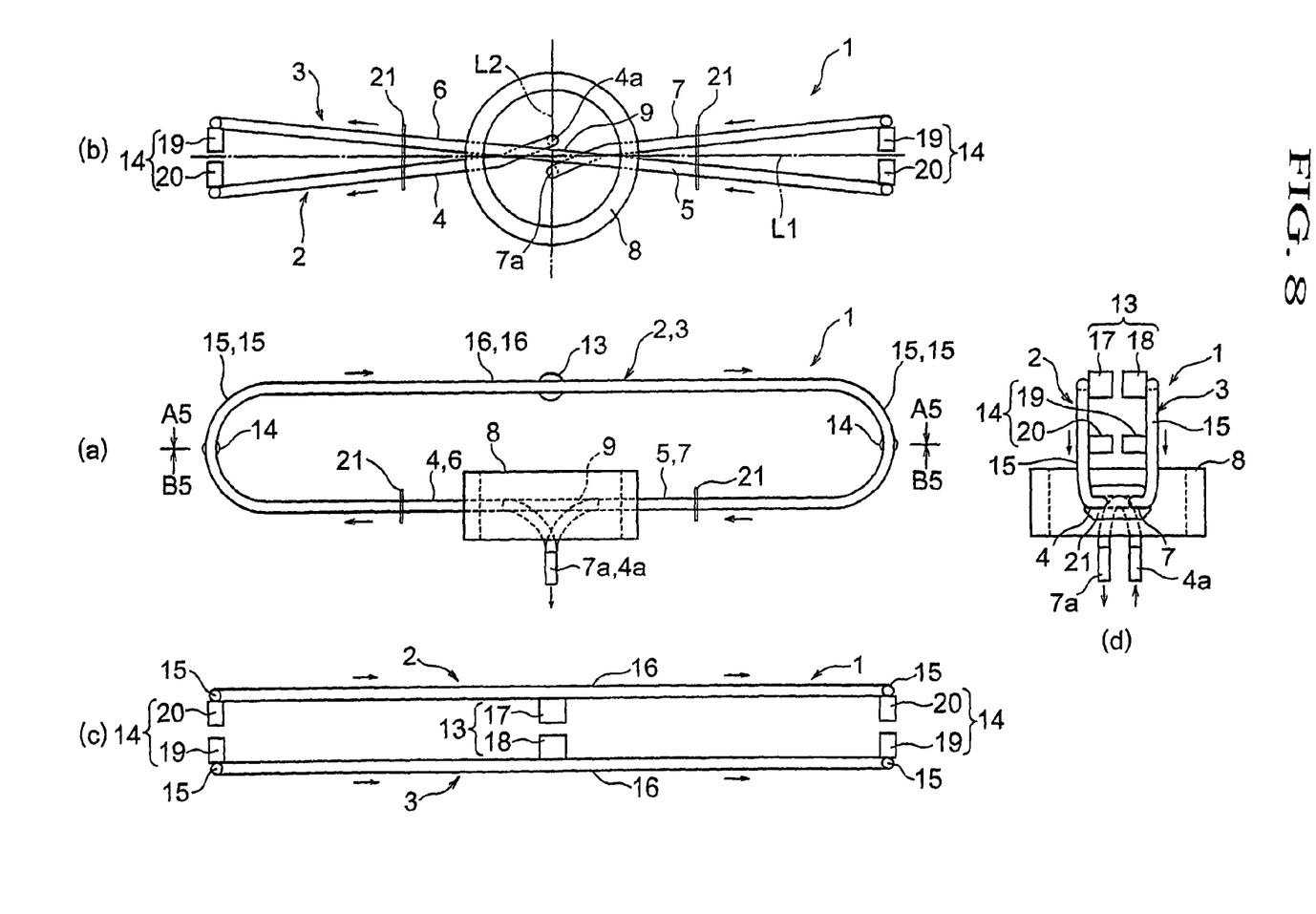

In the flow tube 1 shown in FIGS. 7(a) through 7(d), the lead-out directions of the terminal 4a of the first inlet portion 4 and the terminal 7a of the second outlet portion 7 of the flow tube 1 shown in FIGS. 4(a) through 4(d) are changed. Thus, the terminal 4a of the first inlet portion 4 and the terminal 7a of the second outlet portion 7 shown in FIG. 7 are led out such that, as shown in FIG. 7(a), the direction in which the measurement fluid flows in (terminal 4a) and the direction in which the measurement fluid flows out (terminal 7a) are the same (the vertical direction: see the arrow P of FIG. 1). Further, the first curved tube portion 2 with the terminal 4a of the first inlet portion 4 and the second curved tube portion 3 with the terminal 7a of the second outlet portion 7 are led out so as to be arranged, while undergoing bending as shown in FIG. 7(b), in the center line L2 perpendicular to the center line L1 of the first curved tube portion 2 and the second curved tube portion 3 as shown in FIG. 7(b).

Example 5

In the flow tube 1 shown in FIGS. 8(a) through 8(d), the bending directions of the terminal 4a of the first inlet portion 4 and the terminal 7a of the second outlet portion 7 of the flow tube 1 shown in FIGS. 7(a) through 7(d) are changed.

Example 6

In FIGS. 9(a) through 9(d), a flow tube 1' includes two tube portions: a first curved tube portion 2' and a second curved tube portion 3'. The first curved tube portion 2' has a first inlet portion 4' and a first outlet portion 5'. The second curved tube portion 3' has a second inlet portion 6' and a second outlet portion 7'.

Figure 9:
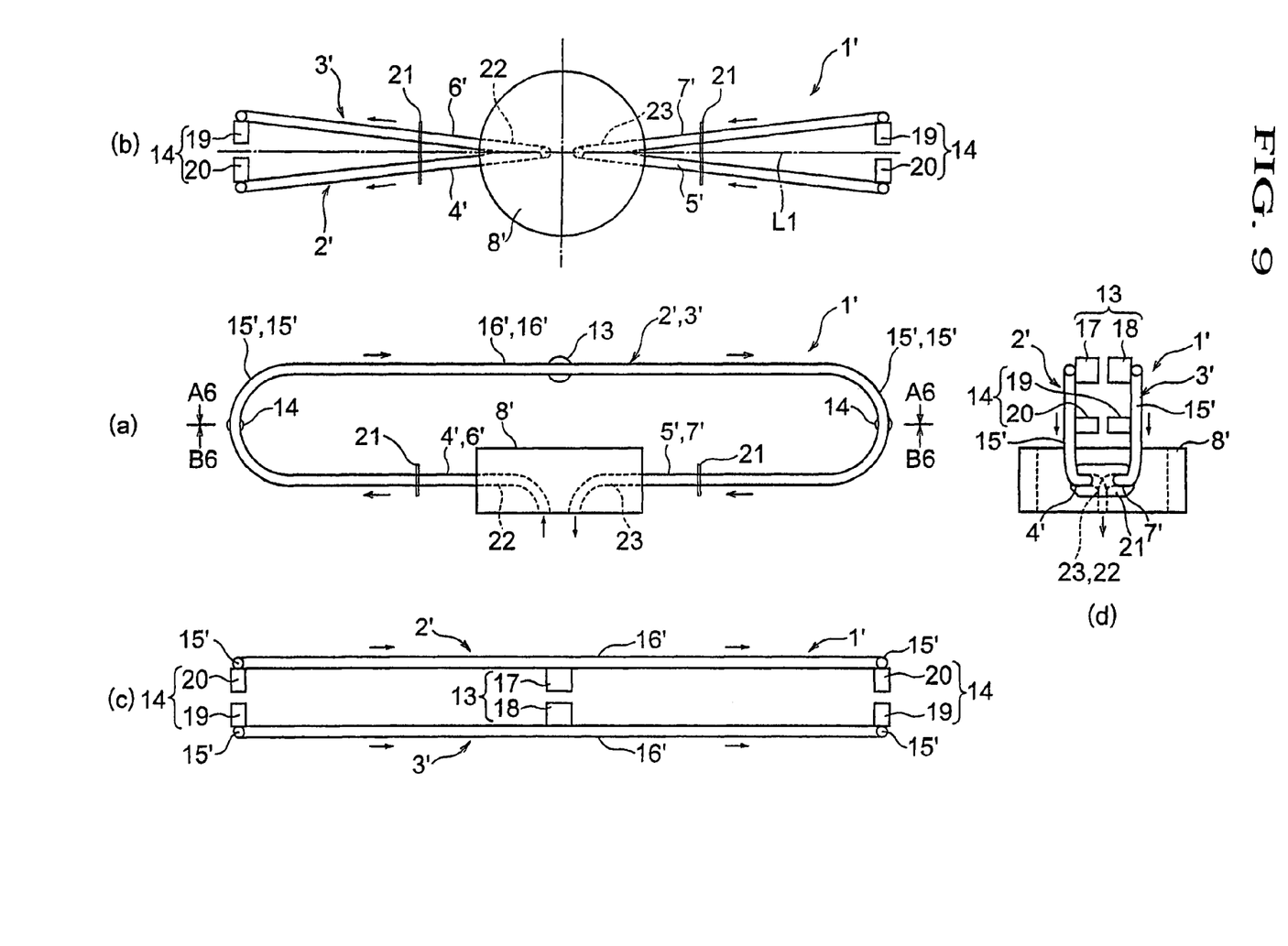

The first inlet portion 4' and the second inlet portion 6' are fixed to a manifold 22 of a fixing member 8' so as to be in the same plane with the first inlet portion 4' and the second inlet portion 6' being arranged so as not to be parallel to each other. Like the first inlet portion 4' and the second inlet portion 6', the first outlet portion 5' and the second outlet portion 7' are fixed to the manifold 22 of the fixing member 8' so as to be in the same plane, with the first outlet portion 5' and the second outlet portion 7' being arranged so as not to be parallel to each other. The measurement fluid flows into the manifold 22 of the fixing member 8'. Further, the measurement fluid flows out through a manifold 23 of the fixing member 8'.

In the flow tubes 1 shown in FIGS. 4 through 10, the driving device 13 is provided between the apex portions 16, 16, 16', and 16' of the first curved tube portion 2 and 2' and the second curved tube portion 3 and 3'. Further, the vibration detecting sensors 14 and 14 are provided between the curved portions 15, 15, 15', and 15' of the first curved tube portions 2 and 2' and the second curved tube portion 3 and 3'. The brace bar 21 is provided to the first inlet portion 4 and 4' and the second inlet portion 6 and 6' so as to be astride the first inlet portion 4 and 4' and the second inlet portion 6 and 6'. Further, the brace bars 21 are spaced apart from the fixing members 8 and 8' by a predetermined distance so as not to come into contact with the fixing members 8 and 8'. Note that, the arrows in FIGS. 4 through 10 show how the measurement fluid flows.

It goes without saying that various modifications are possible without departing from the scope of the present invention.

The invention claimed is:

1. A Coriolis flowmeter for obtaining at least one of a mass flow rate and a density of a measurement fluid through detection of at least one of a phase difference and a vibration frequency proportional to the Coriolis forces acting on a first curved tube portion and a second curved tube portion constituting a measurement flow tube by vibrating the first curved tube portion and the second curved tube portion while being opposed to each other, said Coriolis flowmeter comprising:

a first inlet portion through which the measurement fluid flows in and a first outlet portion through which the measurement fluid flows out, in the first curved tube portion;

a second inlet portion through which the measurement fluid flows in and a second outlet portion through which the measurement fluid flows out, in the second curved tube portion;

a fixing member situated in a middle position of the flow tube when looking down at said Coriolis flowmeter;

the first inlet portion, the second inlet portion, the first outlet portion, and the second outlet portion being fixed to the fixing member; and in the fixation to the fixing member, tube axes of the first inlet portion, the second inlet portion, the first outlet portion, and the second outlet portion are arranged in the same plane, the first inlet portion and the second inlet portion being arranged in a non-parallel state such that a distance therebetween increases as they depart from the fixing member, the first outlet portion and the second outlet portion being arranged in a non-parallel state such that a distance therebetween increases as they depart from the fixing member, and the first inlet portion and the second inlet portion, and the first outlet portion and the second outlet portion are arranged symmetrically.

2. A Coriolis flowmeter according to claim 1, wherein the fixing member is formed substantially in one of a circular configuration and an arcuate configuration when looking down at said Coriolis flowmeter.

3. A Coriolis flowmeter according to claim 2, wherein the fixing member is formed in a wall-like configuration.

4. A Coriolis flowmeter for obtaining at least one of a mass flow rate and a density of a measurement fluid through detection of at least one of a phase difference and a vibration frequency proportional to the Coriolis forces acting on a first curved tube portion and a second curved tube portion constituting a measurement flow tube by vibrating the first curved tube portion and the second curved tube portion while being opposed to each other, said Coriolis flowmeter comprising:
- a first inlet portion through which the measurement fluid flows in and a first outlet portion through which the measurement fluid flows out, in the first curved tube portion;
- a second inlet portion through which the measurement fluid flows in and a second outlet portion through which the measurement fluid flows out, in the second curved tube portion;
- a fixing member situated in a middle position of the flow tube when looking down at said Coriolis flowmeter;
- the first inlet portion, the second inlet portion, the first outlet portion, and the second outlet portion being fixed to the fixing member;
- a connecting tube portion provided between and connecting the first outlet portion and the second inlet portion,
- in the fixation to the fixing member, the first inlet portion and the second inlet portion are arranged in a non-parallel state such that a distance therebetween increases as they depart from the fixing member, the first outlet portion and the second outlet portion being arranged in a non-parallel state such that a distance therebetween increases as they depart from the fixing member, and the first inlet portion and the second inlet portion, the first outlet portion and the second outlet portion being arranged symmetrically; and
- the first outlet portion, the second inlet portion, and the connecting tube portion being arranged such that tube axes of the first outlet portion, the second inlet portion, and the connecting tube portion are in a straight line.

5. A Coriolis flowmeter according to claim 4, wherein the fixing member is formed substantially in one of a circular configuration and an arcuate configuration when looking down at said Coriolis flowmeter.

* * * * *